(12) United States Patent
Chang et al.

(10) Patent No.: US 11,596,790 B2
(45) Date of Patent: Mar. 7, 2023

(54) PAIN MANAGEMENT SYSTEM, METHOD AND DEVICE USING ANALYTICS DRIVEN RANDOM ELECTRICAL STIMULI

(71) Applicant: Calmare Therapeutics, Inc., Fairfield, CT (US)

(72) Inventors: Sin-Min Chang, Fairfield, CT (US); Santanu Das, Fairfield, CT (US); Dae H. Han, Fairfield, CT (US)

(73) Assignee: Calmare Therapeutics, Inc., Fairfield, CT (US)

( * ) Notice: Subject to any disclaimer, the term of this patent is extended or adjusted under 35 U.S.C. 154(b) by 57 days.

(21) Appl. No.: 16/543,708

(22) Filed: Aug. 19, 2019

(65) Prior Publication Data

US 2020/0246618 A1 Aug. 6, 2020

Related U.S. Application Data

(63) Continuation of application No. 15/585,991, filed on May 3, 2017, now Pat. No. 10,384,062.

(60) Provisional application No. 62/241,991, filed on Nov. 3, 2016.

(51) Int. Cl.
*A61N 1/36* (2006.01)
*A61N 1/04* (2006.01)

(52) U.S. Cl.
CPC ........ *A61N 1/36021* (2013.01); *A61N 1/3603* (2017.08); *A61N 1/0456* (2013.01); *A61N 1/36034* (2017.08)

(58) Field of Classification Search
CPC .............. A61N 1/36021; A61N 1/3603; A61N 1/36034; A61N 1/0456
See application file for complete search history.

(56) References Cited

U.S. PATENT DOCUMENTS

| 8,380,317 | B2 | 2/2013 | Marineo |
| 9,037,248 | B2 | 5/2015 | Durand |
| 2007/0025608 | A1* | 2/2007 | Armstrong ......... A61N 1/36071 382/132 |
| 2007/0027497 | A1 | 2/2007 | Parnis |
| 2007/0066971 | A1 | 3/2007 | Podhajsky |

(Continued)

FOREIGN PATENT DOCUMENTS

| JP | 2009-505689 A | 2/2009 |
| JP | 2015-506792 A | 3/2015 |

OTHER PUBLICATIONS

Search and Examination Report dated Jan. 3, 2018 in PCT/US2017/58369 (14 pages).

*Primary Examiner* — Joseph M Dietrich
(74) *Attorney, Agent, or Firm* — McDonnell Boehnen Hulbert & Berghoff LLP

(57) ABSTRACT

Systems, methods, and devices for treating chronic pains effectively are disclosed. The system is based on the use of randomly generated non-pulsed waveform between a frequency of 5 Hz to 2 KHz. The waveforms generated have characteristics which are pre-defined or based on the input and feedback provided by the patient and/or by the clinician, at the same time conforming to certain safety rules and precautions ensuring patient safety. This disclosure also describes a novel approach of implementing a secure memory stick which can be used to exchange data securely between one device and another device where device could be the device mentioned earlier, an off-line server, or a PC.

20 Claims, 10 Drawing Sheets

(56) References Cited

U.S. PATENT DOCUMENTS

| | | |
|---|---|---|
| 2010/0069736 A1 | 3/2010 | Finneran |
| 2012/0022612 A1 | 1/2012 | Littlewood |
| 2013/0138193 A1 | 5/2013 | Durand |
| 2014/0228701 A1 | 8/2014 | Chizeck |

* cited by examiner

PAIN MANAGEMENT SYSTEM, METHOD AND DEVICE USING ANALYTICS DRIVEN RANDOM ELECTRICAL STIMULI

CROSS REFERENCE TO RELATED APPLICATIONS

This application is a continuation of and claims priority to U.S. application Ser. No. 15/585,991, titled "A Novel Pain Management System, Method & Device Using Analytics Driven Random Electrical Stimuli," filed on May 3, 2017, and currently pending. U.S. application Ser. No. 15/585,991 claims priority to U.S. App. 62/416,991, titled "A Novel Pain Management System, Method & Device Using Analytics Driven Random Electrical Stimuli," filed on Nov. 3, 2016. The entire contents of the 15/585,991 and 62/416,991 applications are incorporated herein by reference.

FIELD

This disclosure describes novel methods, systems, and devices for producing and applying electrical stimulation to patients to alleviate chronic pains.

SUMMARY

The word "pain" is used to describe a wide range of unpleasant sensory and emotional experiences associated with actual or potential tissue damages. Nature has made sure that pain is a signal we cannot ignore. According to a 2015 study of the American Academy of Pain Science, there are 116 million U.S. adults who suffer from chronic pain daily. The number of patients affected by pain is larger than those of cancer, diabetes and heart disease combined.

Pain can be categorized into "acute pain" and "chronic pain." Acute pain arises from activation of nociceptors for a limited time and is not associated with significant tissue damage (e.g., a pin prick). Chronic pain, on the other hand, is prolonged pain lasting for months or longer that arises from tissue injury, inflammation, nerve damage, tumor growth, lesion or occlusion of blood vessels. Some well described ailments like herniated disk, rheumatoid and osteoarthritis are known to induce chronic pain, as described in John H. Byrne, NEUROSCIENCE ONLINE: AN ELECTRONIC TEXTBOOK FOR THE NEUROSCIENCES|DEPARTMENT OF NEUROBIOLOGY AND ANATOMY—THE UNIVERSITY OF TEXAS MEDICAL SCHOOL AT HOUSTON, MCGOVERN MEDICAL SCHOOL, Section 2, Chapters 6, 7, 8, available at http://neuroscience.uth.tmc.edu/ ("U. of Texas Health")

John Bonica explains that chronic pain is "exclusively malefic because it is powerfully destructive of the physical and psychological well being of the individual and his or her family and associates, and has no redeeming features." Havi Carel & Rachel Cooper, HEALTH, ILLNESS AND DISEASE: PHILOSOPHICAL ESSAYS (2014), p. 152. One possible explanation for chronic pain is a phenomenon called "sensitization" in nociceptive neurons.

Sensitization results from continuous and prolonged noxious stimulation when silent nociceptive neurons which were previously unresponsive become responsive. In addition, some of the chemicals produced and released at the injured site are believed to also alter the physiological properties of nociceptors. The nociceptors begin to initiate pain signals spontaneously, which cause chronic pain. Weak stimuli, such as a light touch that previously had no effect on these nociceptors, further activate the nociceptors which result in severe pain signals.

There are two classes of fibers which can conduct the sense of pain into a patient's brain: $A\delta$ fibers and C fibers.

$A\delta$ fibers are larger (2-5 mm) in diameter, myelinated, have a fast conduction velocity (5-40 meter/s), and carry information mainly from the nociceptive-mechanical or mechanothermal-specific nociceptors. Their receptive fields are small; thus, they provide precise localization of pain.

C fibers are smaller (0.4-1.2 mm) in diameter, unmyelinated, have a slow conduction velocity (0.5-2.0 meter/s), and are activated by a variety of high-intensity mechanical, chemical and thermal stimulation and carry information from polymodal nociceptors. C fibers comprise about 70% of all the fibers carrying noxious inputs. The receptive field of these neurons is large and, thus, less precise for pain localization, as described in U. of Texas Health.

Pains are carried by both $A\delta$ and C fibers through multiple pathways. The first pathway to be activated is the neospinothalamic pathway, which is carried by fast action $A\delta$ fibers. It is responsible for the immediate awareness of a painful sensation and for awareness of the exact location of the painful stimulus. Several seconds later, paleospinothalamic pathway and archispinothalamic pathway which are carried by C fibers are activated. These pathways stimulate different areas in the brain cortex than neospinothalamic pathways. C fibers involved pathways mediate emotional, cognitive, and autonomic reactions to pain.

The brain has endogenous substances which modulate pain. They activate a class of receptors called opioid receptors. The various types of opioid receptors are distributed differently within the central and peripheral nervous system. Endogenous opioid peptides interact with the opiate receptors to produce analgesia, as described in (i) Stratton, Steven A. "Role of Endorphins in Pain Modulation." *Journal of Orthopaedic & Sports Physical Therapy* 3, no. 4 (1982): 200-05. doi:10.2519/jospt.1982.3.4.200 ("Stratton") and (ii) Ossipov, M. H., G. O. Dussor, and F. Porreca. "Central modulation of pain." *Journal of Clinical Investigation*, Nov. 1, 2010, 3779-787. doi:10.1172/JCI43766 ("Ossipov et al.").

Currently, the most common clinically used drugs for producing temporary analgesia and relief from pain are the opioid family, which includes morphine, and heroin. However, there are several side effects which result from opiate use including tolerance and drug dependence (addiction). In general, these drugs modulate the incoming pain information in the spinal and central sites, relieving pain temporarily.

[13] Besides analgesic drugs like opioids, pain can be relieved through other means like the use of electrical stimulations. For example, Transcutaneous Electrical Nerve Stimulation ("TENS") devices use electrical stimulation to relieve pain. TENS devices are based on "Gate Control" theory, as described in (i) U.S. Pat. No. 8,380,317 ("Marineo '317"); (ii) Marineo, Giuseppe, Vittorio Iorno, Cristiano Gandini, Vincenzo Moschini, and Thomas J. Smith. "Scrambler Therapy May Relieve Chronic Neuropathic Pain More Effectively Than Guideline-Based Drug Management: Results of a Pilot, Randomized, Controlled Trial." *Journal of Pain and Symptom Management* 43, no. 1 (2012): 87-95. doi:10.1016/j.jpainsymman.2011.03.015 ("Marineo et al."); (iii) Coyne, Patrick J., Wen Wan, Patricia Dodson, Craig Swainey, and Thomas J. Smith. "A Trial of Scrambler Therapy in the Treatment of Cancer Pain Syndromes and Chronic Chemotherapy-Induced Peripheral Neuropathy." *Journal of Pain & Palliative Care Pharmacotherapy* 27, no.

4 (2013): 359-64. doi:10.3109/15360288.2013.847519 ("Coyne et al."); and (iv) U. of Texas Health.

Gate control theory postulates that non-painful input closes the gates to painful input, which results in prevention of the pain sensation from traveling to the Central Nervous System (CNS). A TENS device produces electrical signals to stimulate nerves via electrodes attached to patients at electric current levels below the pain threshold that can be tolerated by the patient. This class of devices has been found to be somewhat effective in producing short-term reduction of pain. However, TENS devices have not been found to be effective in treating chronic pain.

In contrast to TENS devices, Scrambler theory-based electrical stimulation has been found to be effective in treating chronic neuropathic pain, as described in Marineo et al. and Coyne et al. Devices based on scrambler theory use a synthetic waveform for electrical stimulation. The idea is to assemble synthetic action potentials, similar to endogenous action potential waveforms, to create streams of "non-pain" information to modulate the pain signal being transmitted to the patient's CNS.

As discussed, electrical stimulation of nerves carrying pain signals has been used to attempt to attenuate the sensation of pain. These include Spinal Cord Stimulation ("SCS"), Transcutaneous Electrical Stimulation ("TENS") discussed earlier, Percutaneous Electrical Stimulation ("PENS"), and Peripheral Nerve Field Stimulation ("PNFS"). These techniques are thought to operate by inducing parasthesia, or a pins and needles sensation, which overwhelms much of the pain response but is not thought to inhibit transmission of the pain signals. The sensation of parasthesia simply masks the pain so it is less evident to the patient. But this effect gets reduced over time, as the patient becomes acclimated to the parasthesia and begins to notice once again the underlying pain. In addition, parasthesia itself can be unpleasant, and in some patients, it may actually exacerbate the perception of pain, as described in U. of Texas Health.

As mentioned earlier, chronic pain is prolonged pain lasting for months or longer that arises from tissue injury, inflammation, nerve damage, tumor growth, lesion, or occlusion of blood vessels. Chronic or inflammatory pain can sensitize the nervous system, evoking chemical, functional, and even structural changes that serve to "prime the pain processing pump." Chronic pain, such as lower back pain, rheumatoid and osteoarthritis, and headache may result from constant inflammatory activity which activates receptors. In some cases, the pain persists long after the injury heals, but there is no treatment that will eliminate the pain.

Sensation of pain comes in two phases, as described in U. of Texas Health. The first phase is mediated by the fast-conducting Aδ fibers and the second part due to (Polymodal) C fibers. The pain associated with the Aδ fibers is typically associated with an initial extremely sharp pain. The second phase is a more prolonged and slightly less intense feeling of pain as a result of the acute damage. If there is massive or prolonged input to a C fiber, there is a progressive build up in the spinal cord dorsal horn; this phenomenon is similar to tetanus in muscles but is called wind-up, as described in Li, Jun, Donald A. Simone, and Alice A. Larson. "Windup leads to characteristics of central sensitization." Pain 79, no. 1 (1999): 75-82. doi:10.1016/s0304-3959(98)00154-7. ("Li et al.") If wind-up occurs there is a probability of increased sensitivity to pain. This increased sensitivity is closely related to "sensitization" mentioned earlier which causes chronic pain.

U.S. Pat. No. 9,037,248 ("Durand '248") discloses blocking electrical nerve signals by the use of a cuff apparatus through which a transverse electrical current is applied to block pain signals traveling through the smaller, unmyelinated C-fibers. Durand '248 recommends the use of non-pulsed electrical stimulus having a frequency between 10 Hz to 2 KHz through the cuff apparatus. The efficacy of the approach in Durand '248 was verified by having the scheme used with a rabbit by stimulating directly the sural nerve with a non-pulsed signal. The Durand '248 approach establishes the efficacy of using non-pulsed waveforms to block pain signals traveling through C fibers. However, one drawback of the approach in Durand '248 is the use of a specialized "cuff" apparatus.

Using current techniques like those used in TENS devices to induce parasthesia to mask the pain signals might affect the transmission characteristics of larger fibers responsible for higher sensory and motor functions, and even activate those fibers causing involuntary muscle contractions (spasm) and other sensory side effects, as pointed out in Durand '248. Thus, it is desirable to inhibit, e.g. block, the transmission of pain signals through the small, unmyelinated fibers that principally carry them without substantially affecting the larger fibers responsible for higher sensory and motor functions.

Durand '248 discloses that electrical stimulation using a non-pulsed waveform can avoid activating the larger nerve fibers (such as Aα, Aβ and Aδ). Conventional TENS devices use pulses within a frequency range of 50 Hz to 100 Hz having sharp rise times, which triggers A fibers, whereas stimulation with a signal having a slow rise time within a frequency range of 10 Hz to 2 KHz triggers activation of C fibers, while avoiding activation of A fibers.

The inventors of this disclosure believe that, for longer-term pain management, it is desirable to target and trigger only the C fibers instead of both A and C fibers.

This disclosure describes novel methods, systems, and devices for producing electrical stimulation to alleviate chronic pains. In some embodiments, the device produces electrical stimulation in the frequency range of 5 Hz to 2 KHz using non-pulsed waveforms to increase the likelihood that only the C fibers are targeted and triggered to produce longer term analgesia to relieve pain. In operation, the electrical stimulation is highly probabilistic where the probability profile can be selected from a fixed set of profiles or the profile can be dynamically adjusted by another algorithm chosen by a clinician or patient. In some embodiments, the therapy device applies electrical stimulation via electrodes placed on dermatomes close to the patient's pain region but not on the patient's pain region itself. Depending on the nature of the pain and the history of the patient, multiple pairs of electrodes might be used by the clinician. The C fibers in this approach are stimulated directly by placing the electrodes on dermatomes close to the pain region and no additional "cuff" apparatus is required.

In other embodiments, instead of generating the waveforms using probabilistic methods, the stimulus signal can alternatively be created from a plurality of waveforms chosen from a database. In some embodiments, the database of waveforms includes non-pulsed waveforms like sinusoidal, triangular, trapezoidal, or other non-pulsed waveforms. In some embodiments, the database of waveforms includes atomic waveforms like the ones shown and described in Marineo '317.

In operation, the stored waveforms can be used in such a way that the RMS value is within a range selected by a clinician or selected by the system based on a patient's input or the clinician's input or a combination of both, always making sure that safety limits for applied voltage and current are obeyed, while at the same time applying an adequate level of stimuli sufficient to treat patients.

This disclosure also describes a novel approach of implementing a secure memory stick system. By using a secure memory stick, patient data can be transported securely and exchanged securely between one device and another device where the devices could be a pain management system, an off-line server, a PC, or other computing device.

This overview is illustrative only and is not intended to be limiting. In addition to the illustrative aspects, embodiments, and features described herein, further aspects, embodiments, and features will become apparent by reference to the figures and the following detailed description. The features and advantages of the disclosed systems and methods, as well as other aspects, advantages, and alternatives will become apparent to those of ordinary skill in the art by reading the following detailed description, with reference where appropriate to the accompanying drawings.

DETAILED DESCRIPTION OF THE DRAWINGS 1.1.1 Example Waveform Construction Procedures As discussed above, disclosed herein are systems, devices, and methods for generating and applying electrical stimulation therapy signals to patients. In some embodiments, a therapy device includes one or more processing elements, circuitry configured to generate and apply electrical stimulation signals to a patient via one or more sets of electrodes, and tangible, non-transitory computer-readable media comprising instructions stored therein, wherein the instructions, when executed by the one or more processing elements, cause the therapy device to perform functions comprising: (i) generating one or more random electrical stimulation signals in a frequency range between about 5 Hz and about 2 KHz, wherein an individual random electrical stimulation signal is based on a plurality of randomly-generated non-pulsed waveforms; and (ii) applying the one or more random electrical stimulation signals to a patient via the circuitry.

Some embodiments further include the therapy device generating the plurality of randomly-generated non-pulsed waveforms. In some embodiments, generating the plurality of randomly-generated non-pulsed waveforms comprises, for an individual waveform: (i) determining one or more waveform attributes for the waveform and (ii) generating the waveform according to the one or more determined waveform attributes. In some embodiments, the waveform attributes comprise (i) a random number of segments for the waveform, (ii) a random positive peak voltage for the waveform, (iii) a random location in the waveform for the positive peak voltage, (iv) a random negative peak voltage for the waveform, (v) a random location in the waveform for the negative peak voltage, (vi) a random location in the waveform for each waveform segment, and (vii) a random slope for each waveform segment. In some embodiments, an individual randomly-generated non-pulsed waveform may additionally or alternatively comprise (i) a positive peak voltage that is limited to a maximum positive peak voltage, and (ii) a negative peak voltage that is limited to a maximum negative peak voltage.

Figure 1:
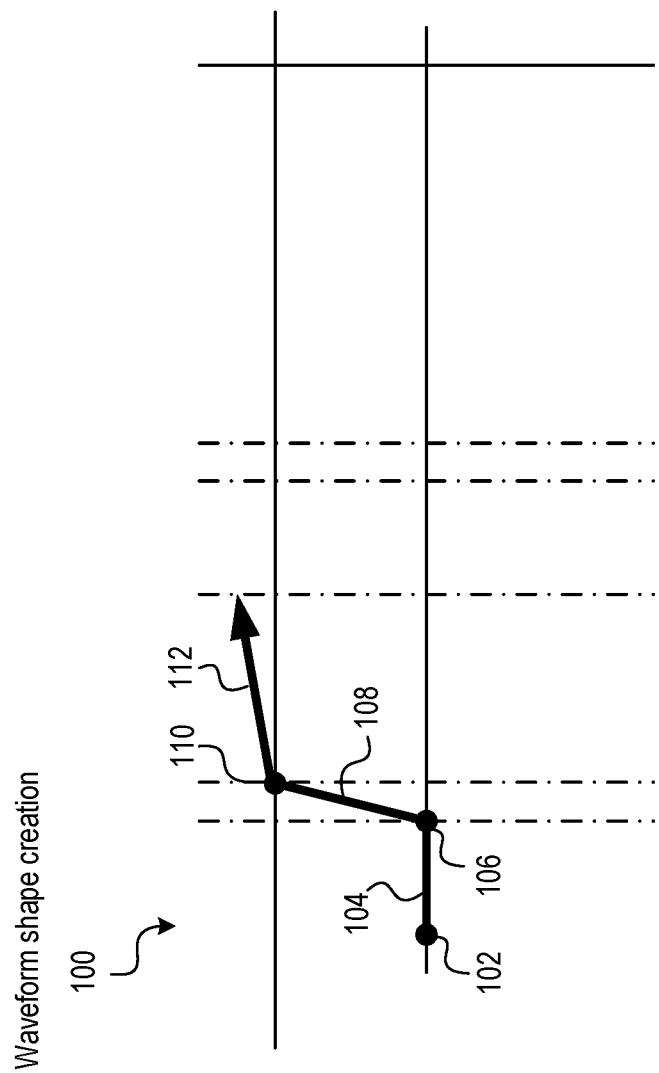
FIG. 1 shows aspects of an example waveform shape creation process according to some embodiments.

FIG. 1 shows an example waveform shape creation according to some embodiments. The classical linear equation has the form Y=mx+c, where m is the slope of the line and c is the intercept.

In some embodiments, the waveforms are constructed in segments, where each segment is a line with the starting point (x, y) which is varied. The slope m, length (l) of the segment, and the intercept c may also be varied. For example, the parameters l and m are varied randomly within a range while the initial value of c is defined in a random manner. The subsequent values, c, in a particular cycle of waveform are defined automatically. The constructed peak amplitude of the waveform is again varied in a random manner while keeping the RMS voltage of each waveform within a configurable range.

FIG. 1 illustrates aspects of the above-described approach, where the example waveform 100 has a plurality of segments 104, 108, and 112. Each segment has a randomly selected starting point (x, y) and intercept c. For example, segment 104 has starting point 102, segment 108 has starting point 106 and intercept, and segment 112 has starting point 110 and intercept. Each segment also has a corresponding randomly selected length, l. Each segment's randomly selected (x, y) starting point, c, and length (l) are combined to create an individual waveform.

In some embodiments, the waveform generation procedure can follow a set of rules, and any unspecified variables can be assigned using a random number when a decision is required to create the waveform. For example, some embodiments use one or more rules selected from a set of rules for creating waveforms comprising:

1. Only one positive peak followed by one negative peak.
2. The waveform starts at 0 and ends at 0.
3. Before the positive peak is reached, all slopes in each segment should be positive or no less than 0 and the slopes are limited not to be too steep (less than a specific value).
4. After the positive peak is reached, all slopes should be negative.
5. After the negative peak is reached, all slopes should be positive or 0.

6. Slopes are limited so that the rise time cannot be too steep.
7. After the negative peak is reached, the amplitude cannot be positive (cannot be above 0).
8. If a maximum value (positive) is reached before the designated positive peak location, the amplitude remains at the maximum value until the time of the designated positive peak value.
9. If a minimum value (negative) is reached before the designated negative peak location, the amplitude remains at the minimum value until the time of the designated negative peak value.

Figure 2:
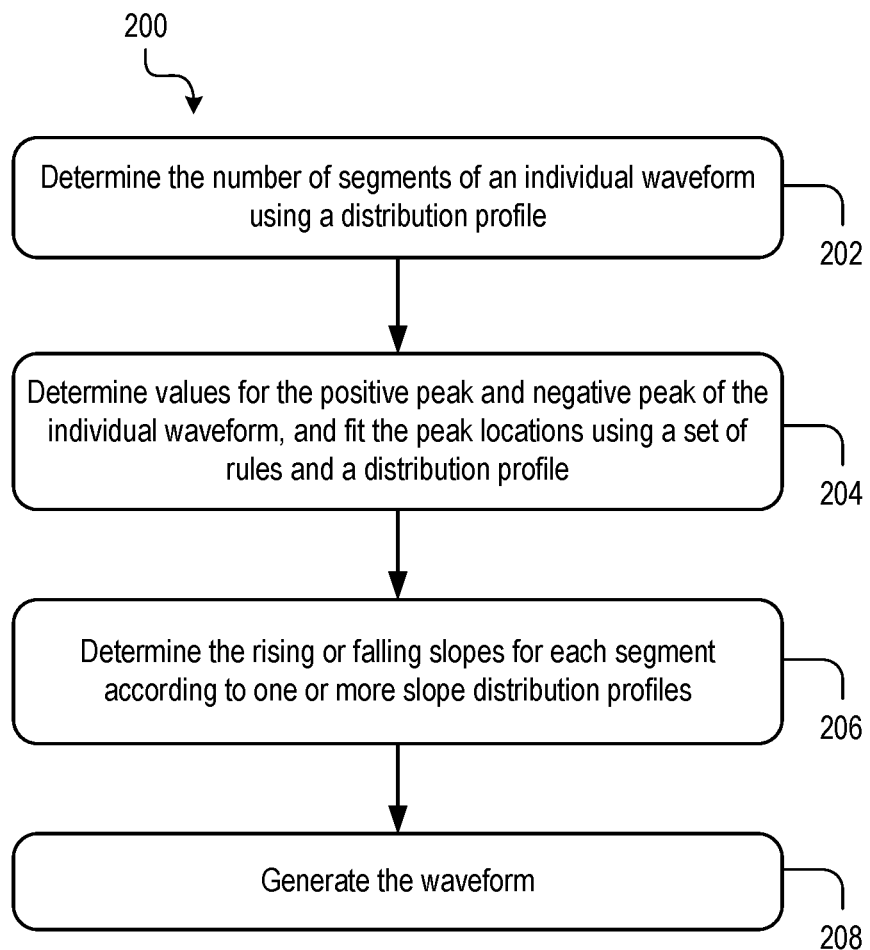
FIG. 2 shows an example process for randomly generating a waveform according to some embodiments.

FIG. 2 shows an example process 200 for randomly generating a waveform according to some embodiments. In some embodiments, process 200 can be used for generating a waveform such as waveform 100 shown and described with reference to FIG. 1.

Process 200 begins at step 202, which includes determining the number of segments of an individual waveform using a distribution profile. Process 200 assumes there will be one positive peak followed by one negative peak. As a result, there will be at least 3 segments in the entire waveform. In operation, however, a waveform could have any number of segments, e.g., 4, 5, 6, 7, 8, 9, or even 10 or more segments.

Figure 3:
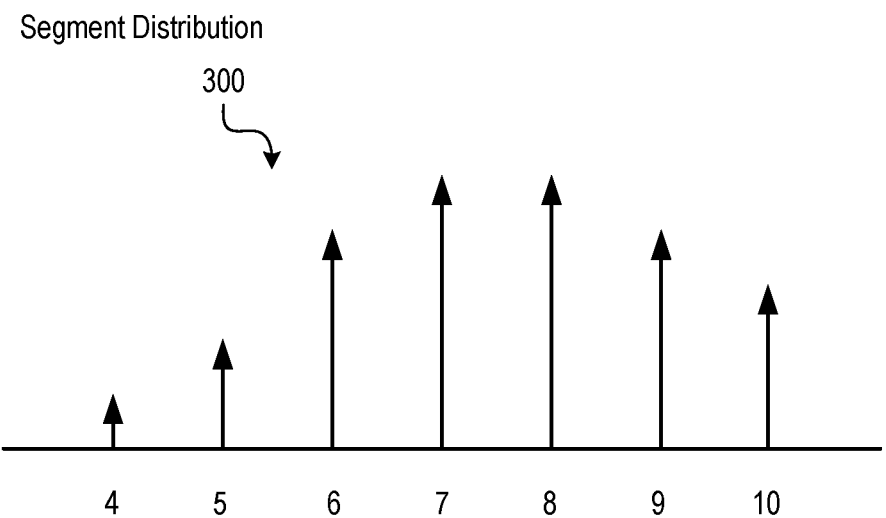
FIG. 3 shows an example of number of segments distribution according to some embodiments.

In some embodiments, the number of segments for an individual waveform can be determined by using a random number generator with a specific distribution profile. FIG. 3 shows an example segment distribution profile 300 for randomly generating the number of segments for an individual waveform according to some embodiments, where the values in the distribution profile correspond to the number of segments in the individual waveform.

After determining the number of segments for an individual waveform in step 202, process 200 next advances to step 204, which includes (i) determining values for the positive peak and negative peak of the individual waveform, and (ii) fitting the peak locations using a set of rules and a distribution profile.

Figure 4:
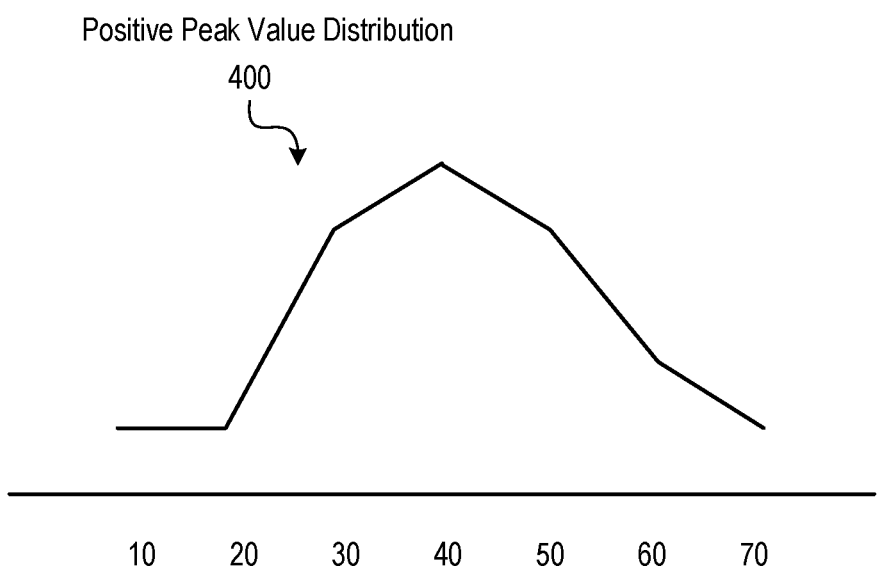
FIG. 4 shows an example of positive peak location distribution according to some embodiments.
Figure 5:
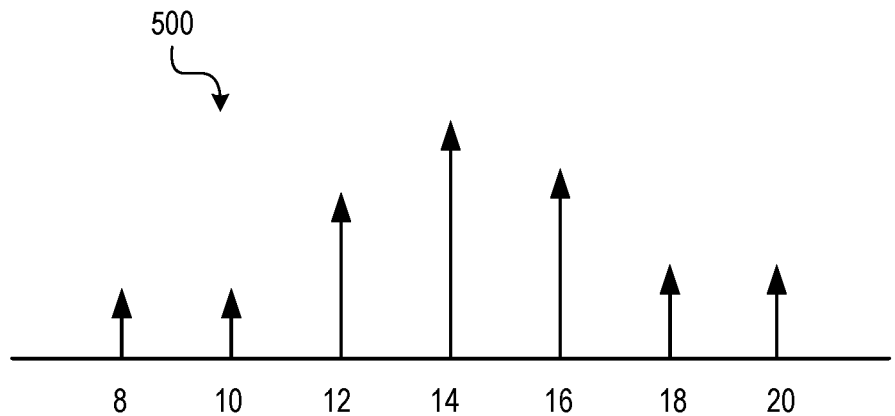
FIG. 5 shows an example distance between positive and negative peaks probability distribution according to some embodiments.

In some embodiments, values for the positive peak and negative peak of the individual waveform can be determined according to one or more distribution profiles. FIG. 4 shows an example distribution 400 of positive peak values according to some embodiments, where the values in the distribution profile correspond to peak voltages for the individual waveform. Once the positive peak value is determined, the negative peak value can be determined based on a random difference between the positive and negative peaks. FIG. 5 shows an example distribution 500 of differences between the positive peak and the negative peak for use in determining the negative peak value for the individual waveform, where the values in the distribution profile correspond to a difference in voltage between the positive peak and the negative peak of the waveform. The locations of the remaining segment boundaries can be determined by a random process with uniform distribution for example, according to one or more rules, such as the rules described above with reference to FIG. 1.

Process 200 then advances to step 206, which includes determining the rising or falling slopes for each segment of the waveform. In operation, slopes before the positive peak have a positive slope (or rising slope) and the slopes after the positive peak have a negative slope (or falling slope).

Figure 6:
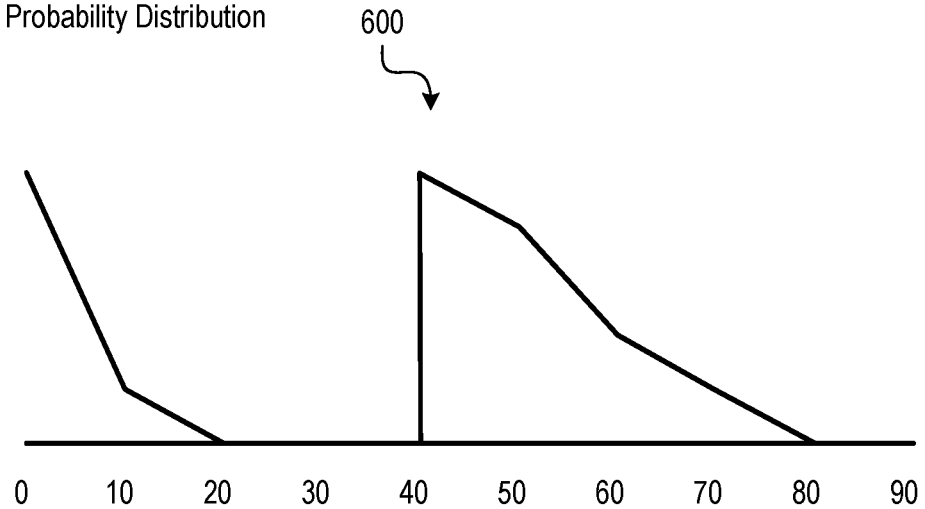
FIG. 6 shows an example of the rising slope probability distribution according to some embodiments.

In some embodiments, the rising and falling slopes can be determined by a random process according to one or more probability distribution profiles. FIG. 6 shows an example slope probability distribution 600 according to some embodiments, where each value in the profile corresponds to a slope angle (0-90 degrees) for slopes for segments before the positive peak. For segments before the positive peak, all the slopes are non-negative (0 to 90 degrees); however, fast rising slopes could be avoided by using a distribution profile like profile 600, which shows an example of the rising slope probability distribution according to some embodiments. In operation, using a distribution profile like profile 600 to generate waveforms results in non-pulsed waveforms because none of the rising slopes are greater than 80 degrees, as shown in profile 600. In some embodiments, the distribution profile is arranged so that each waveform generated by the procedure will have a rise time that is greater than about 10 microseconds.

Waveform segments after the positive peak will have a negative slope value. Some embodiments can use another slope probability distribution profile (not shown) for the slopes for the segments after the positive peak for the waveform. Some embodiments could alternatively use profile 600 for the segments after the positive peak, but with each slope angle having a negative value.

After completing steps 202-206, process 200 advances to step 208, where the individual waveform is generated. In some embodiments, the therapy system uses the waveform to generate an electrical stimulation signal that is applied to the patient.

In some embodiments, the therapy device may additionally or alternatively store the generated waveform in a waveform database. In operation, in some embodiments, the therapy system generates many individual waveforms according to process 200, combines the individual waveforms into a time-series of waveforms, and then uses the time-series of waveforms to generate the electrical stimulation signal that the therapy system applies to the patient.

Thus, in this manner, the therapy system generates a random electrical stimulation signal based on a plurality of non-pulsed waveforms, where the individual waveforms of the plurality of waveforms are randomly-generated according to process 200. In operation, the therapy system applies the random electrical stimulation signal to the patient at frequencies within a range of about 5 Hz to about 2 kHz. For at least some patients, applying this random electrical stimulation signal based on the plurality of non-pulsed waveforms at frequencies between about 5 Hz to about 2 kHz preferably triggers only the patient's the C fibers instead of the patient's A and C fibers, thereby having a therapeutic effect for the patient by reducing one or more of the patient's chronic pain symptoms.

In some embodiments, the therapy system also controls an individual electrical stimulation signal to have a randomized root-mean-square ("RMS") voltage between a configurable lower RMS voltage and a configurable upper RMS voltage.

The RMS value of a set of values (or a continuous-time waveform) is the square root of the arithmetic mean of the squares of the values, or the square of the function that defines the continuous waveform. The RMS current is the "value of the direct current that dissipates power in a resistor."

In the case of a set of n values $\{x_1, x_2, \ldots x_n\}$, the RMS value is:

$$x_{rms} = \sqrt{\frac{1}{n}(x_1^2 + x_2^2 + \cdots + x_n^2)}$$

In operation, after constructing a waveform, the therapy system computes the RMS value, and if the RMS value so computed does not match with the intended value (i.e., if the RMS value is outside of the range of the configured lower RMS voltage and upper RMS voltage), then the therapy system adjusts the RMS value by adjusting the values of $x_1$, through $x_n$ to control the RMS value to be between the configured lower and upper RMS voltage range.

In some embodiments, at least one of the lower RMS voltage and the upper RMS voltage of the random electrical stimulation signal for the patient is based at least in part on an analysis of a plurality of quantitative pain metrics for the patient. In some embodiments, the quantitative pain metrics include answers to a detailed pain assessment questionnaire, such as the one at https://www.painedu.org/DOwnloads/NIPC/Pain_Assessment_Scales.pdf, the contents of which are incorporated herein by reference. Other pain assessment questionnaires with different pain assessment questions could alternatively be used as well.

In some embodiments, a clinician can conduct the analysis of the patient's answers to the questions and then determine appropriate settings for a patient's therapy session, including but not necessarily limited to one of the upper or lower RMS voltage for the electrical stimulation signals that the therapy device applies to the patient. The clinician then configures the therapy device with the determined upper and/or lower RMS voltage values.

In other embodiments, the therapy device (or perhaps a computing device associated with the therapy device) can conduct the analysis of the patient's answers to the questions and then determine appropriate settings for the patient's therapy session, including but not necessarily limited to one of the upper or lower RMS voltage for the electrical stimulation signals applied to the patient.

In some embodiments, regardless of whether the clinician (individually or in combination with another computing device associated with the therapy device) determines the upper and/or lower RMS voltage values, the corresponding range of RMS voltage values is set by the therapy device automatically at a range of RMS voltage levels expected to be effective for treating a chronic pain symptom for the patient. This range of RMS voltage levels expected to be effective for treating a chronic pain symptom for the patient is determined based on analytics and/or a learning algorithm implemented by the therapy device and/or a computing device associated with the therapy device. Inputs for the analytics are based on the patient's feedback on the effectiveness of past therapy sessions (where applicable), the patient's answers to the pain assessment questionnaire, the patient's medical history, past therapy setting, and/or treatment history/experience with patients having similar medical history, chronic pain symptoms, therapy success, etc.

In some embodiments, the therapy system is further configured to control the random electrical stimulation signals to also limit RMS current applied to the patient so that the RMS current applied to the patient is less than or equal to a configurable maximum RMS current limit. In operation, controlling the RMS current in this manner prevents the electrical signals from causing harm or discomfort to the patient, or at least substantially reduces the likelihood that the electrical signals will cause harm or discomfort to the patient.

1.1.2 Example Therapy System

Figure 7:
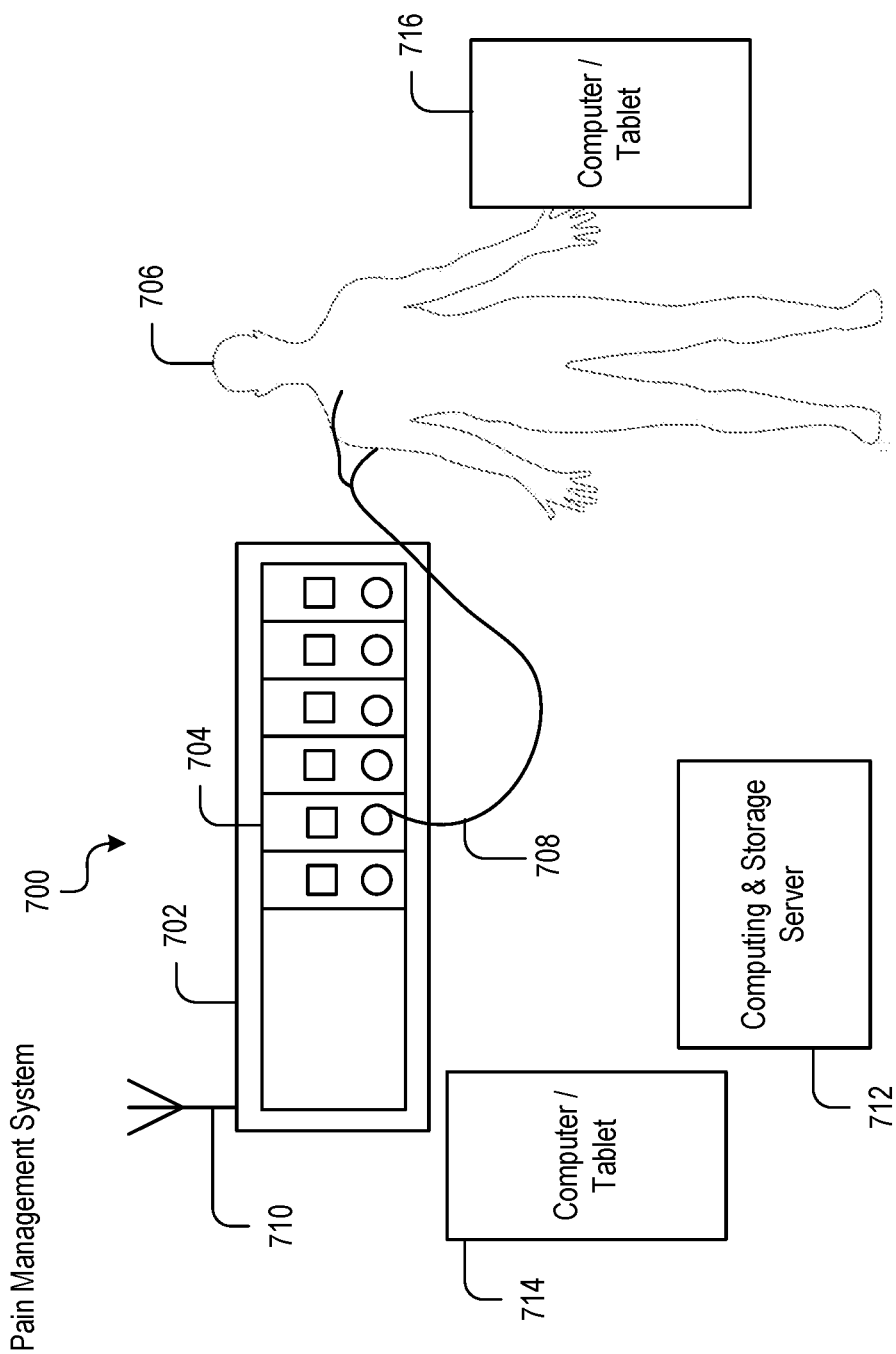
FIG. 7 shows an example therapy system according to some embodiments.

FIG. 7 shows an example therapy system 700 according to some embodiments.

The system 700 includes a therapy device 702, a computing and storage server 712, and one or more computer/tablet devices 714, 716.

In operation, the therapy device 702 includes one or more channel modules 704 that generate and apply electrical stimulation signals to a patient 706 via one or more sets of electrodes 708. The therapy device 702 also includes one or more wireless and/or wired communication interfaces 710 that enables the therapy device 702 to communicate with the computing and storage server 712 and the one or more computer/tablet devices 714, 716.

A number of stake holders and devices other than the therapy device 702 could be involved with and play a role in the treatment process, including (i) clinicians, (ii) the patient 706, (iii) the one or more computer/tablet devices 714, 716 used by clinicians and the patient 706, and (iv) the computing and storage server 712 for provisioning the therapy and for storing therapy data collection and analytics.

In a typical scenario, the clinician attaches electrodes 708 to the patient 706. The electrodes are placed on the dermatomes close to the patient's pain region, but avoiding the actual location of the pain itself. Depending on the patient's history and past treatment results, the clinician might choose to use multiple electrode pairs. After the electrodes 708 are attached to the patient 706, the clinician operates the therapy device 702 either through the device's on-device control interfaces or through a computer/hand-held device 714. In operation, the computer/tablet 714 could be any type of desktop computer, laptop computer, portable computing device (e.g., a tablet or smartphone), or any other type of computing device now known or later developed. In some embodiments, the patient 706 provides information, such as answers to questions or other feedback to help the clinician determine aspects of the patient's 706 therapy, such as where to affix the electrodes 708 and characteristics of the electrical stimulation signal applied to the patient 706, such as the intensity of the stimulation signal, the duration of the therapy session, and perhaps other aspects.

In some embodiments, the patient provides the answers to the questions and/or other feedback for use by the clinician in planning and administering the patient's 706 therapy through computing device 716, which could be any type of desktop computer, laptop computer, portable computing device (e.g., a tablet or smartphone), or any other type of computing device now known or later developed. In some instances, the clinician may help the patient 706 to provide the feedback, answers, and other information using clinician's computer or tablet 714. One example of a questionnaire to solicit information from the patient 706 for setting the parameters of the patient's therapy is the questionnaires described in NIPC, "Pain Assessment Scales," available at https://www.painedu.org/DOwnloads/NIPC/Pain_Assessment_Scales.pdf, the contents of which are incorporated herein by reference. The intensity of the stimulation signal can be varied manually by the clinician using potentiometers on (or at least associated with) each channel module 704 that is configured to apply the electrical stimulation signal (therapy signal) to the patient 706. In operation, the therapy device 702 has the capability to override and adjust the intensity level set by the clinician if the therapy device 702 determines the clinician's selected intensity level might be unsafe or may otherwise cause harm or discomfort to the patient. In some embodiments, the therapy device 702 (alone or in combination with an associated computing device) determines whether to override and adjust a clinician's selected intensity level based at least in part on one or more of the patient's feedback on the effectiveness of past therapy sessions (where applicable), the patient's answers to the pain assessment questionnaire, the patient's medical history, past therapy setting, and/or treatment history/experience with patients having similar medical history, chronic pain symptoms, therapy success, etc.

In some embodiments, the therapy device 702 receives one or more of an upper RMS voltage level setting, a lower RMS voltage level setting, and a maximum RMS current level setting for one of the one or more random waveforms. In response to receiving the settings, the therapy device 702 determines whether any of the received upper RMS voltage level setting, lower RMS voltage level setting, and maximum RMS current level setting would, if implemented, either (i) increase a likelihood that the electrical stimulation signal will cause the patient to experience pain or discomfort or (ii) reduce a likelihood that the electrical stimulation signal will be effective for treating a chronic pain symptom for the patient, as described above. And in response to determining that at least one of the received upper RMS voltage level setting, lower RMS voltage level setting, and maximum RMS current level setting would, if implemented, increase a likelihood that the electrical stimulation signal will cause the patient to experience pain or discomfort or reduce the likelihood that the electrical stimulation signal will be effective for treating a chronic pain symptom for the patient, the therapy device 702 overrides at least one of the received upper RMS voltage level setting, lower RMS voltage level setting, or maximum RMS current level setting with a corresponding different setting determined to one or both (i) not increase a likelihood that the electrical stimulation signal will cause the patient to experience pain or discomfort or (i) not reduce the likelihood that the electrical stimulation signal will be effective for treating a chronic pain symptom for the patient.

In some embodiments, records of a therapy session are stored in tangible, non-transitory computer-readable memory of any of (i) the therapy device 702, (ii) the computing and storage server 712 associated with the therapy device 702, (iii) the clinician's computer/tablet 714, and/or (iv) the patient's computer/tablet 716. In operation, the inter-connection of the therapy device 702 with any of the computing and storage server 712 or computer/tablets 714, 716 for control, computing and storage with the therapy device 702 can be accomplished via one or more wireless and/or wired communication interfaces 710.

For example, the wireless interface could include WiFi, Bluetooth, or any other wireless communications protocol now known or later developed that is sufficient for transmitting/receiving command and control information and transferring configuration and therapy history data between the therapy device 702 and any other computing device, such as the computing and storage server 712, computer/tablets 714, 716, or any other computing device now known or later developed. Similarly, the wired interface could include Ethernet, USB connection, or any other wired communications protocol now known or later developed that is sufficient for transmitting/receiving command and control information and transferring configuration and therapy history data between the therapy device 702 and any other computing device, such as the computing and storage server 712, computer/tablets 714, 716, or any other computing device now known or later developed.

In some embodiments, the patient's computer/tablet 716 is preferably a secure device so that an un-approved (or at least unsecure) computing device cannot be attached to the therapy device 702. For example, some embodiments include the use of a secure USB dongle to transmit/receive therapy session configuration settings and/or therapy session history information to/from the therapy device 702, as described herein with reference to FIGS. 11 and 12.

In operation, some embodiments of the therapy device 702 use method 200 shown and described in Section 1.1.1 and with reference to FIGS. 1-6 to create the individual waveforms that the therapy device 702 uses for generating the electrical stimulation signal(s) that the therapy device 702 applies to the patient 706 via the one or more sets of electrodes 708. In some embodiments, the therapy device 702 may generate an electrical stimulation signal based on the individual waveforms substantially in real time as the waveforms are generated, e.g., generating an electrical signal corresponding to the waveform substantially contemporaneously with generating the waveform. For example, the therapy device 702 in some embodiments may generate an electrical stimulation signal based on the waveforms on the order of a few microseconds or milliseconds after generating the waveform.

In other embodiments, the therapy device may store the waveforms generated according to method 200 in tangible non-transitory computer readable memory on the therapy device 702, and then generate an electrical stimulation signal based on the stored waveforms. In operation, electrical stimulation signal generation can be a very short time after waveform generation (e.g., a few seconds or minutes) or a comparatively long time after waveform generation (e.g., a few minutes to a few hours or even days). For example, the waveforms for a particular patient's therapy session could be generated in advance by the therapy device 702 and stored in tangible, non-transitory computer readable memory, and then downloaded from the memory for use in generating the electrical stimulation signals applied to the patient 706. Other embodiments may additionally or alternatively include the computing and storage server 712 generating waveforms according to method 200 and then downloading the generated waveforms to the therapy device 702 for use by the therapy device 702 in generating the electrical stimulation signals applied to the patient 706.

In some embodiments, the therapy device 702 generates the electrical stimulation signal applied to the patient 706 during a therapy session by (i) combining a plurality of the randomly-generated non-pulsed waveforms into a time series and then (ii) generating the electrical simulation signal based on this series of randomly-generated non-pulsed waveforms.

In some embodiments, the electrical stimulation signal generated by the therapy device 702 during a therapy session includes multiple active and inactive periods. During an active period, the therapy device 702 applies a signal to the patient, while during an inactive period, the therapy device 702 does not apply any signal to the patient. In operation, each active period may be anywhere from a few milliseconds to a few seconds, and similarly, each inactive period may be anywhere from a few milliseconds to a few seconds. In this manner, the electrical stimulation signal applied to the patient in such embodiments is effectively "turned on and off" during these relatively short (e.g., about 500 ms to about 10 s) alternating active and inactive periods during the therapy session.

In some embodiments, the therapy device 702 (i) randomly selects a duration for each active period and (ii) randomly selects a duration for each inactive period. In some embodiments, the selected duration for each active period is within a configurable active period duration range defined by a configurable lower active period limit and a configurable upper active period limit. And in some embodiments, the selected duration for each inactive period is within a configurable inactive period duration range defined by a configurable lower inactive period limit and a configurable upper inactive period limit.

For example, assume the active period duration is configured with a lower active period limit of 1.5 seconds and an upper active period limit of 8 seconds, and an inactive period duration is configured with a lower inactive period limit of 0.05 seconds and an upper inactive period limit of 2 seconds. In such a configuration, the electrical stimulation signal (therapy signal) generated by the therapy device 702 would comprise alternating active and inactive periods, where each active period has a randomly-selected duration of 1.5 to 8 seconds and each inactive period has a randomly-selected duration of 0.05 to 2 seconds. In operation, the duration of each active period and each inactive period can be selected according to a random number generator and/or according to a probability distribution similar to the ones shown and described elsewhere herein. And during each active period, the electrical stimulation signal is based on a plurality of randomly-generated non-pulsed waveforms as described above.

Although the example above uses an active period of duration of 1.5 to 8 seconds and an inactive period duration of 0.05 to 2 seconds, other ranges could be used instead. In some embodiments, the active period duration range and the inactive period duration range is configurable by a clinician or the patient. In some embodiments, the ranges for the active and inactive periods may be ranges determined (or at least expected) to be effective for treating one or more of the patient's chronic pain symptoms based at least in part on a clinician's assessment of one or more of the patient's feedback on the effectiveness of past therapy sessions (where applicable), the patient's answers to the pain assessment questionnaire, the patient's medical history, past therapy setting, and/or treatment history/experience with patients having similar medical history, chronic pain symptoms, therapy success, etc.

In some embodiments, the active and inactive period duration ranges are additionally or alternatively configurable by the therapy device 702. In some embodiments, the therapy device 702 automatically configures the active and inactive period duration ranges to ranges it has determined (or at least expects) to be effective for treating one or more of the patient's chronic pain symptoms based at least in part on the therapy system's 700 analysis of one or more of the patient's feedback on the effectiveness of past therapy sessions (where applicable), the patient's answers to the pain assessment questionnaire, the patient's medical history, past therapy setting, and/or treatment history/experience with patients having similar medical history, chronic pain symptoms, therapy success, etc.

In some embodiments, the data stored in the memory of the therapy device 702 (individually or in combination with memory of the computing and storage server 712 and/or computer/tablets 714, 716), including control settings for the therapy device 702 and patient and clinician personal information and responses, can be analyzed and correlated with other therapy records. In operation, this data can be analyzed and correlated with other therapy records for the purpose of improving the therapy treatment and identifying misdiagnosis.

Pain could result from common causes, diseases, or injuries. In operation, any one or more of the clinician, the therapy device 702, and/or the computing and storage server 712 (individually or in combination) can identify patterns of pain relief and corresponding therapy device 702 configuration settings that are more effective at treating a particular patient's chronic pain symptoms based at least in part on (i) the clinician's assessment of the patient's condition and/or symptoms, (ii) the patient's feedback to therapy sessions (e.g., did the patient experience any improvement in chronic pain symptoms), and/or (iii) the patient's answers to pain assessment questions, such as questions to a pain assessment questionnaire like the ones described herein. These assessments by the clinician, therapy device 702, and/or computing and storage server 712 can be made before, during, and after a therapy session, as needed.

In some embodiments, the therapy device 702 (individually or in combination with the computing and storage server 712) can compare clinician assessment, patient feedback, and/or questionnaire answers for a first patient with a database of clinical assessments, patient feedbacks, and/or questionnaire answers for other patients. Such a comparison could be useful for at least two reasons.

First, such a comparison could be used to see which therapy device 702 configuration settings have proven more effective in treating chronic pain symptoms for other patients to determine (or at least help determine) therapy device 702 configuration settings for the first patient. Second, this comparison could be useful in avoiding therapy device 702 configuration settings that may cause the first patient harm or discomfort before the start of a therapy session.

For example, if other patients with chronic pain symptoms similar to the first patient (based on the clinician's assessment and patient feedback and/or questionnaire answers) have experienced improvement with some configuration settings, but have experienced pain, discomfort, or lack of improvement with other configuration settings, the configuration settings resulting in improvement could be used for the first patient's therapy session while the configuration settings that resulted in pain, discomfort, or lack of improvement could be avoided. Similarly, if the patient has previously experienced pain, discomfort, or lack of improvement with certain configuration settings (even if other patients have experienced improvement with the same configuration settings), the configuration settings that have previously caused the first patient pain, discomfort, or lack of improvement can be avoided in subsequent therapy sessions. Particularly for configuration settings that have caused the first patient pain and discomfort during an earlier therapy session, this capability of the therapy device 702 (individually or in combination with any of the computing and storage server 712 and/or computer/tablets 714, 716) to access a history of therapy outcomes and corresponding therapy device 702 configuration settings for patients is a form of safety precaution of the system 700 not available in prior art electrical stimulation systems to the knowledge of the inventors.

1.1.3 Example Therapy Device

Figure 8:
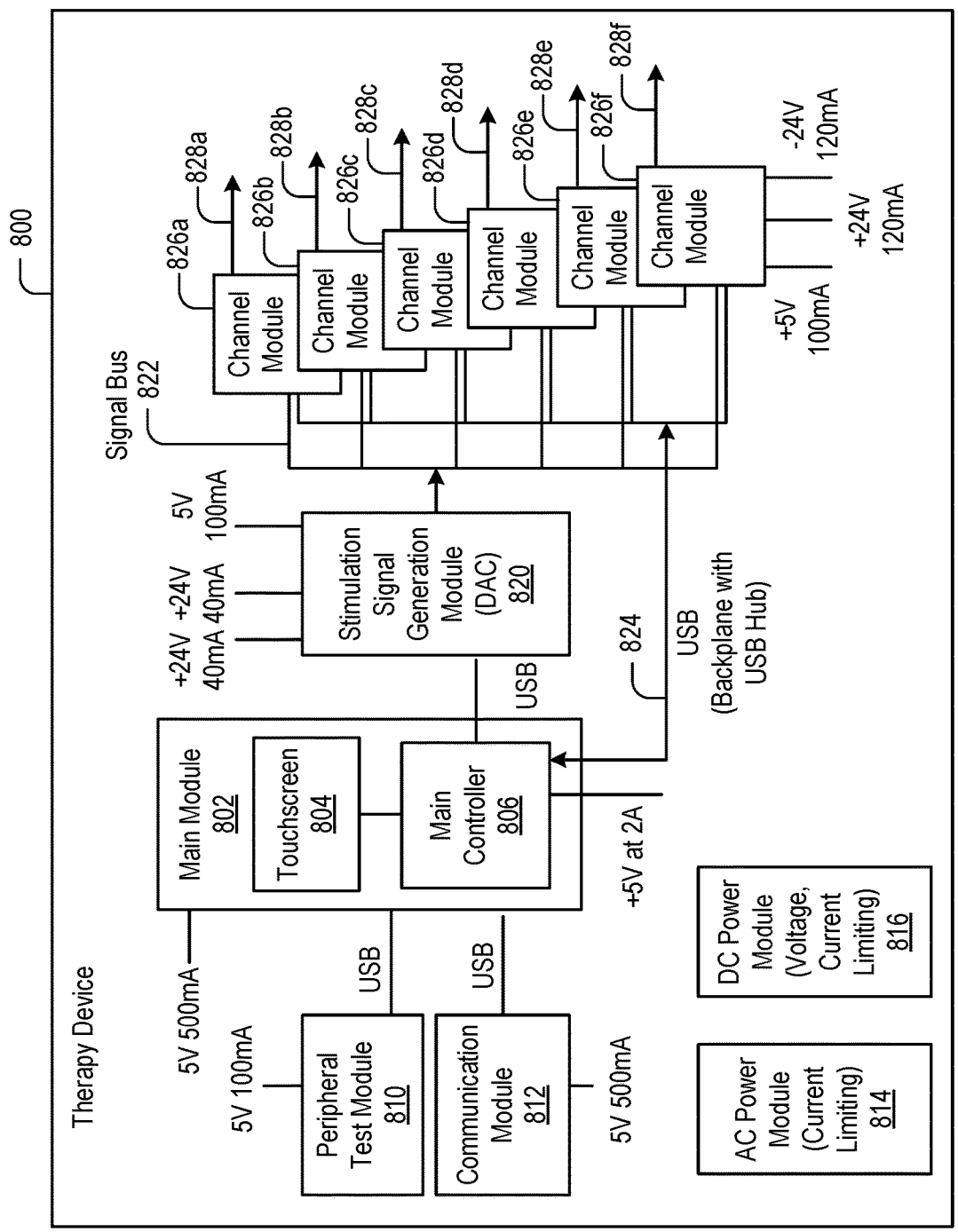
FIG. 8 shows a simplified block diagram of an example therapy device according to some embodiments.

FIG. 8 shows a simplified block diagram of an example therapy device 800 according to some embodiments. Therapy device 800 may be similar to or the same as therapy device 702 shown and described with reference to FIG. 7.

In some embodiments, example therapy device 800 is constructed in the manner shown in FIG. 8 using modular components. Therapy device 800 includes (i) a main module 802 comprising a main controller 806 and a touchscreen 804, (ii) signal generation module 820, (iii) one or more channel modules 826a-f, where each channel module is configured to apply electrical stimulation signals (therapy signals) to a patient via sets of electrodes 828*a-f*, (iv) peripheral test module 810, (v) one or more communication modules 812, (vi) Alternating Current (AC) Power Module 814, (vii) and Direct Current (DC) Power Module 816.

The main module 802 contains the main controller 806. In example therapy device 800, a Universal Serial Bus (UBS) connects the main controller 806 of the main module 802 with the peripheral test module 810, communication module(s) 812, signal generation module 820, and channel modules 828*a-f*, but any other suitable system bus or shelf backplane technology now known or later developed could be used. In some embodiments, the main module 802 may additionally connect to the AC power module 814 and DC power module 816 via the USB bus or other backplane connection for signaling and control. The touchscreen 804 is the main User Interface (UI) for the therapy device 800. In some embodiments, individual channel modules 828*a-f* may additionally include controls for per-channel signal level strength adjustment and perhaps other channel-specific controls.

In operation, the main controller 806 in the main module 802 controls the configuration of therapy signal generation. In some embodiments, the main controller 806 creates a therapy script for a particular electrical stimulation signal to be generated. The therapy script is then provided to the signal generation module 820 where digital information of the therapy script is translated into analog waveforms for generating electrical stimulation signals (therapy signals) according to any of the embodiments disclosed and described herein and having the attributes of any of the embodiments disclosed and described herein.

The signal generation module 820 then broadcasts the analog therapy signal via the signal bus 822 to all the channel modules 826*a-f*. Each channel module 826*a-f* in turn amplifies the received analog therapy signal and applies the therapy signal to the patient via one or more corresponding sets of electrodes 828*a-f*. In some embodiments, each channel module 826*a-f* also regulates one or both of the RMS voltage and/or RMS current of the therapy signal that it applies to the patient.

In some embodiments, an individual channel module controls the RMS voltage of the electrical stimulation signal (therapy signal) applied to the patient to stay within a range of RMS voltage levels defined by a configured lower RMS voltage level and a configured upper RMS voltage level, where the configured range has been determined to be effective for treating one or more of the patient's chronic pain symptoms. In operation, the main controller 806 may determine this range (individually or in combination with one or more external computing devices) through an analysis of historical therapy data and patient outcomes. Alternatively, the main controller 806 may set this range based on an input from a clinician or patient, or based on a configuration input received from an external computing device via the one or more communication module(s) 812.

In some embodiments, an individual channel module may additionally control the RMS current of the electrical stimulation signal (therapy signal) applied to the patient to stay under a configured maximum RMS current level, where the maximum RMS current level has been set to prevent the patient from experiencing pain and/or discomfort during the therapy session. In operation, the main controller 806 may determine this maximum RMS current level (individually or in combination with one or more external computing devices) through an analysis of historical therapy data and patient outcomes. Alternatively, the main controller 806 may set this maximum RMS current level based on an input from a clinician or patient, or based on a configuration input received from an external computing device via the one or more communication module(s) 812.

In some embodiments, one or both of the RMS voltage and/or RMS current of the electrical stimulation signal generated by the channel module can be controlled by the clinician and/or patient via per-channel controls, e.g., via a potentiometer or similar control mechanism. In some embodiments, the main controller 806 may override a maximum RMS voltage and/or maximum RMS current setting that the clinician and/or patient may have selected for an individual channel when the main controller 806 has determined that the selected RMS voltage or RMS current settings (i) may cause the patient pain or discomfort and/or (ii) may be ineffective for treating the patient's chronic pain symptoms. In operation, the main controller 806 may analyze historical therapy data and patient outcomes to determine (i) whether a particular RMS voltage and/or RMS current level may cause the patient pain or discomfort and/or (i) whether a particular RMS voltage and/or RMS current level may be more or less effective for treating a patient's chronic pain symptoms.

Additionally or alternatively, in some embodiments, the main controller 806 can also generate a stimulus signal via the peripheral test module 810 (or a separate cable test module (not shown)) to test a cable. In operation, by observing the returned signal of the test signal through the cable under test via the peripheral test module 810 (or separate cable test module), an undistorted return signal represents a perfect condition for the cable under test while a weak or no return signal represents a defective cable under test. In this manner, the therapy device 800 enables a clinician or patient to test the cables that carry the electrical stimulation signals (therapy signals) from the channel modules 826*a-f* to the sets of electrodes 828*a-f* to ensure that the cables are in good working order for therapy delivery.

1.1.4 Example Channel Module

Figure 9:
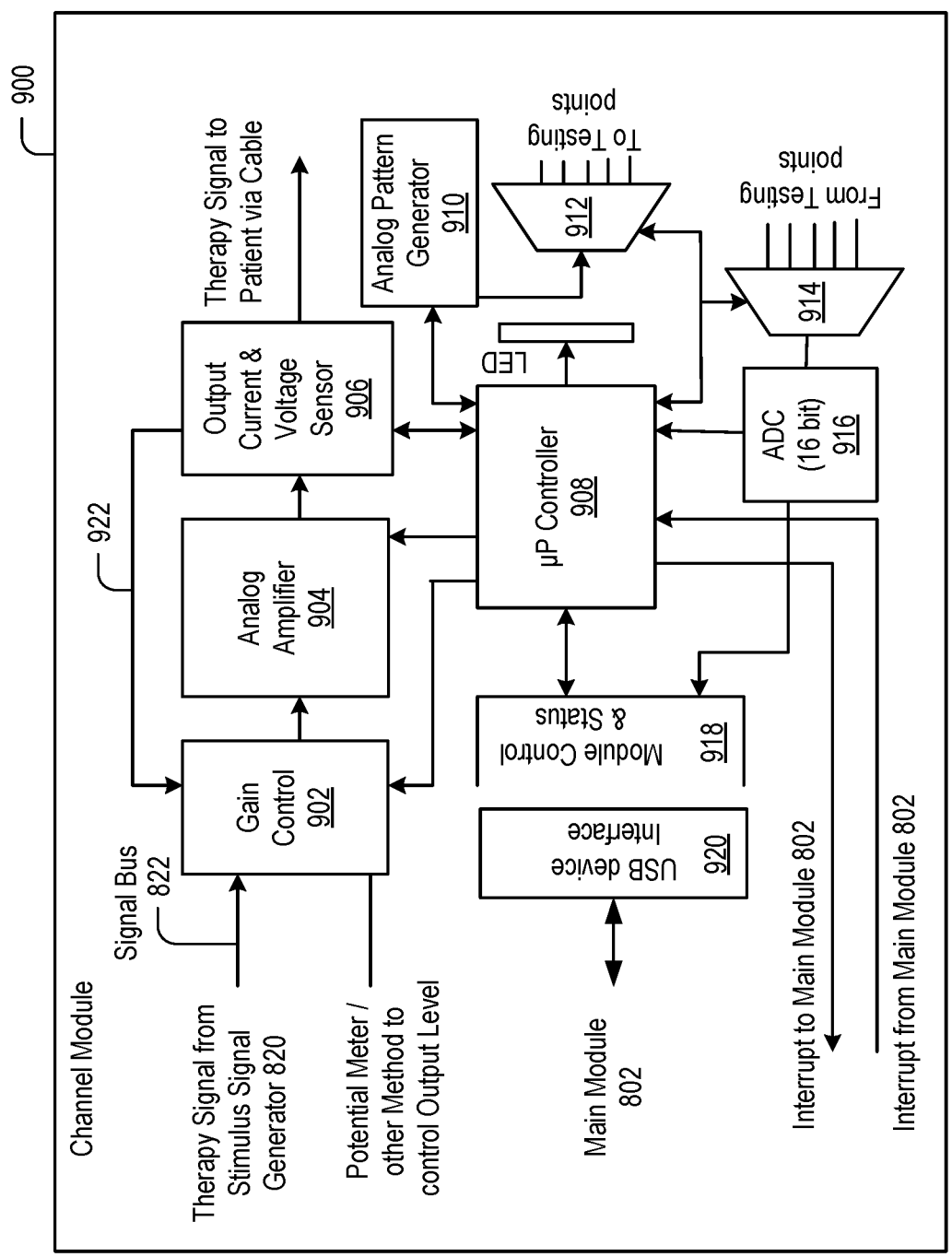
FIG. 9 shows a simplified block diagram of an example channel module according to some embodiments.

FIG. 9 shows a simplified block diagram of an example channel module 900 according to some embodiments. In operation, the example channel module 900 is same as or similar to channel module 704 shown and described with reference to FIG. 7 and/or one of the channel modules 826*a-f* shown and described with reference to FIG. 8.

Channel module 900 includes (i) a gain control block 902 comprising a potentiometer and other circuitry, (ii) analog amplifier 904, (iii) output current & voltage sensor 906, (iv) microcontroller 908, (v) analog pattern generator 910, (vi) a USB interface 920, (vii) an analog to digital converter (ADC) 916, (viii) a testing output interface 912, and (ix) a testing input interface 914.

In operation, channel module 900 receives a therapy signal in analog form via the signal bus 822 from the signal generation module 820 (FIG. 8), amplifies the received signal via the analog amplifier 904, and regulates the current level of the electrical stimulation signal (therapy signal) applied to the patient via a feedback loop 922 from the output current & voltage sensor 906 to the gain control 902. In operation, the output current & voltage sensor 906 (i) measures the RMS value of the output current and RMS value of the output voltage of the electrical stimulation signal (therapy signal) generated by the analog amplifier 904 and (ii) provides a feedback signal 922 to the gain control 902 for controlling the gain of the analog signal input into the analog amplifier 904 for amplification and application to the patient.

In some embodiments, the main controller 806 (FIG. 8) of the main module 802 (FIG. 8) of the therapy device 800 (FIG. 8) sends configuration settings and control signals 918 to the channel module 900 via the USB interface 920, where the channel module 900 serves as a slave device of the main controller 806 (FIG. 8). In operation, the main controller 806 of the main module 802 can send an interrupt signal to the microcontroller 908 of the channel module 900, and the microcontroller 908 of the channel module 900 can trigger an interrupt to the main controller 806 of the main module 802.

The example channel module 900 also provides multiple test points controlled by a USB compatible control register which selects a particular test point for testing. In operation, a specific test pattern is generated by the analog pattern generator 910. The analog test pattern is fed to the test point via the testing output interface 912. The resulting output of the observable signal of the specified test point is then received by the testing input interface 914 and captured for analysis using the ADC 916.

1.1.5 Example Stimulation Signal Generation Module

Figure 10:
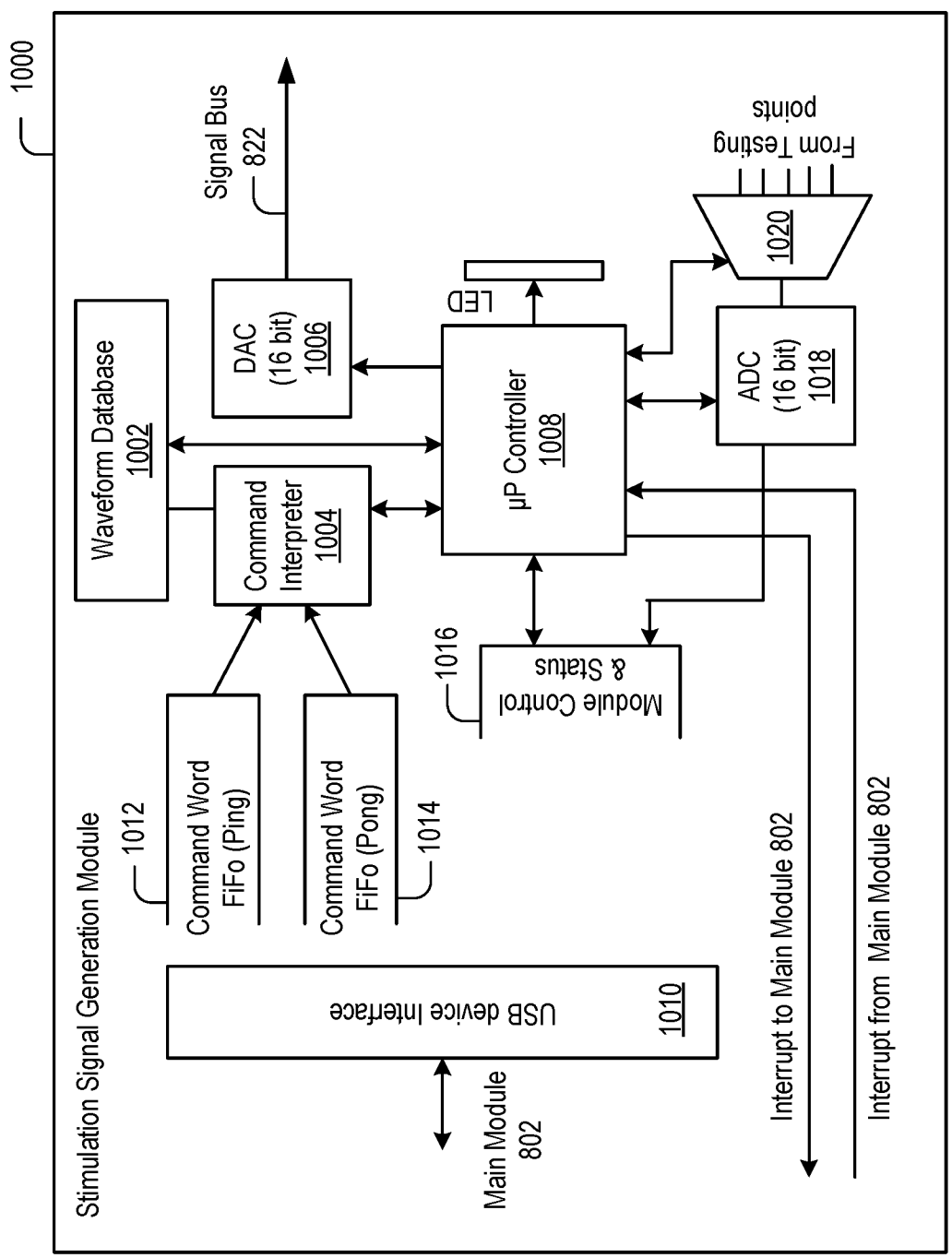
FIG. 10 shows a simplified block diagram stimulation signal generator module according to some embodiments.

FIG. 10 shows a simplified block diagram of a stimulation signal generation module 1000 according to some embodiments. The stimulation signal generation module may be the same as or similar to the stimulation signal generation module 820 shown and described with reference to FIG. 8.

In operation, the stimulation signal generation module 1000 receives therapy information in the form of a digital script from the main module 802 (FIG. 8), converts the received therapy information into an analog therapy signal, and broadcasts the therapy signal to one or more of the channel cards 826a-f (FIG. 8) via a signal bus 822. The stimulation signal generation module 1000 performs these function via a combination of dedicated hardware and microprocessor with flexible firmware.

The example stimulation signal generation module 1000 includes (i) a waveform database 1002, (ii) command interpreter 1004, (iii) a digital to analog converter (DAC) 1006, (iv) a microprocessor/microcontroller 1008, (v) a USB device interface 1010, (vi) a testing input interface 1020, and (vii) an analog to digital converter (ADC) 1018.

The USB device interface 1010 handles communication between the microcontroller 1008 and the main controller 806 (FIG. 8) of the main module 802 (FIG. 8) of the therapy device 800 including control and status messages 1016 and commands for generating waveforms. To handle a large amount of data transferred from the main module 802, the stimulation signal generation module 1000 includes two banks of First-In First-Out (FIFO) buffers which work in conjunction with a dedicated hardware (e.g., Fast Packet Gate Array ("FPGA") of other type of firmware/hardware) and tangible, non-transitory computer readable memories to buffer waveform generation commands 1012, 1014 received from the main module 802 and destined for the command interpreter 1004. When one bank of the FIFO is close to being full or empty, an interrupt can be generated with the interrupt vector available for the main module 802.

In some embodiments, the microprocessor/microcontroller 1008 generates waveforms according to any of the methods disclosed and described herein. In some embodiments, each waveform generated by the microprocessor/microcontroller 1008 has a rise time greater than about 10 microseconds. In some embodiments, the microprocessor/microcontroller 1008 controls an individual waveform to have a randomized RMS voltage between a configurable lower RMS voltage and a configurable upper RMS voltage. In some embodiments, the microprocessor/microcontroller 1008 sets at least one of the lower RMS voltage and the upper RMS voltage of the random waveform for the patient based at least in part on an analysis of a plurality of quantitative pain metrics for the patient. In some embodiments, the microprocessor/microcontroller 1008 sets individual randomly-generated non-pulsed waveforms to have (i) a positive peak voltage that is limited to a maximum positive peak voltage, and (ii) a negative peak voltage that is limited to a maximum negative peak voltage.

The stimulation signal generation module 1000 stores the waveforms generated by the microprocessor/microcontroller 1008 in the waveform database 1002. The stimulation signal generation module 1000 uses the DAC 1006 to convert the generated waveforms stored in the waveform database 1002 into analog signals. In operation, the DAC 1006 can be an 8 or 12 bit or even 16 bit or higher analog to digital converter.

In some embodiments, the microprocessor/microcontroller 1008 monitors intermediate and final analog stimulation signals generated by the DAC 1006 and broadcasted to the channel modules via the signal bus 822. In operation, the microprocessor/microcontroller 1008 selects one or more test input points received via the testing input interface 1020. In some embodiments, the testing input interface 1020 is an analog multiplexer or similar component. The ADC 1018 converts the analog signal received at the selected test input point of the testing input interface 1020 to digital format for processing by the microprocessor/microcontroller 1008 and/or passing to the main module 802 (FIG. 8) via the USB device interface 1010 for analysis.

In some embodiments, and as mentioned earlier, the stimulation signal generation module 1000 may additionally or alternatively store a pre-configured library of non-pulsed waveforms in the waveform database 1002. In some embodiments, rather than generating and storing waveforms in the waveform database 1002, the stimulation signal generation module 1000 may instead receive a library of non-pulsed waveforms via the USB device interface 1010 from the main module 802 (FIG. 8). In some embodiments, the main module 802 may have received the library of non-pulsed waveforms from one or more external computing devices (e.g., the computing & storage server 712 or computer/tablets 714, 716) (FIG. 7).

In such embodiments, the stimulation signal generation module 1000 is configured to generate the electrical stimulation signals (therapy signals) based on the plurality of non-pulsed waveforms stored in the waveform library 1002.

In some embodiments, as described earlier, the non-pulsed waveforms stored in the waveform library 1002 may include sinusoidal, triangular, trapezoidal, or other types of non-pulsed waveforms. In operation, the stimulation signal generation module 1000 randomly selects waveforms from the waveform library 1002 for generating the therapy signals that are applied to the patient.

One or more (or all) of the waveform and therapy signal configurability capabilities of the embodiments where the stimulation signal generation module 1000 randomly generates the waveforms may also be implemented in embodiments where the stimulation signal generation module 1000 randomly selects waveforms from the waveform library 1002. For example, embodiments where the stimulation signal generation module 1000 randomly selects waveforms from the waveform library 1002 may also, in some embodiments, include the capability to configure one or more of (i)

an upper RMS voltage, (ii) a lower RMS voltage, (iii) a maximum RMS current level, (iv) an active period duration range, (v) an inactive period duration range, and/or (vi) any of the other waveform and/or therapy signal configurability capabilities disclosed and described herein. Additionally, any of the upper and lower RMS voltage, maximum RMS current level, active and inactive period duration ranges, and/or any other waveform and/or therapy signal configurations can be configured by a clinician, patient, and/or the therapy system (individually or in combination) based at least in part on an analysis of one or more of the patient's feedback on the effectiveness of past therapy sessions (where applicable), the patient's answers to the pain assessment questionnaire, the patient's medical history, past therapy setting, and/or treatment history/experience with patients having similar medical history, chronic pain symptoms, therapy success, etc., according to any of the methods disclosed and described herein.

The waveform library 102 may additionally or alternatively include a set of atomic waveforms like the ones shown and described in Marineo '317. In some embodiments where the stimulation signal generation module 1000 selects waveforms from a library (e.g., waveform library 1002) as described in Marineo '317, the therapy system may additionally generate and apply electrical stimulation signals (therapy signals) to a patient in substantially the same way as described in Marineo '317.

In some embodiments where the stimulation signal generation module 1000 selects waveforms from a library (e.g., waveform library 1002) as described in Marineo '317, the stimulation signal generation module 1000 may additionally or alternatively implement one or more (or all) of the waveform and therapy signal configurability capabilities of the embodiments where the stimulation signal generation module 1000 randomly generates the waveforms. For example, in some embodiments where the stimulation signal generation module 1000 selects waveforms from the waveform library 1002 in the manner described in Marineo '317 (or otherwise uses waveforms similar to or the same as the ones disclosed in Marineo '317), the therapy system may additionally include the capability to configure one or more of (i) an upper RMS voltage, (ii) a lower RMS voltage, (iii) a maximum RMS current level, (iv) an active period duration range, (v) an inactive period duration range, and/or (vi) any of the other waveform and/or therapy signal configurability capabilities disclosed and described herein. Additionally, any of the upper and lower RMS voltage, maximum RMS current level, active and inactive period duration ranges, and/or any other waveform and/or therapy signal configurations can be configured by a clinician, patient, and/or the therapy system (individually or in combination) based at least in part on an analysis of one or more of the patient's feedback on the effectiveness of past therapy sessions (where applicable), the patient's answers to the pain assessment questionnaire, the patient's medical history, past therapy setting, and/or treatment history/experience with patients having similar medical history, chronic pain symptoms, therapy success, etc., according to any of the methods disclosed and described herein.

1.1.6 Secure Dongle Host Method

In some embodiments, the one or more communication modules 812 (FIG. 8) includes a communications interface that accommodates an external dongle device. In some embodiments, the external dongle device can be attached to the therapy device 800 (FIG. 8) or other host device (e.g., the computing & storage server 712 or computer/tablets 716, 716) through an interface like USB or SCSI.

In operation, a clinician and/or the patient can (i) store patient treatment data (e.g., patient symptoms, treatment history, historical therapy configuration settings, etc.) on the external dongle and/or (ii) transfer patient treatment data between the external dongle and the therapy device or other host device. In some embodiments, the therapy device or other host device validates the dongle device before any patient data is transferred between the dongle and the host.

Figure 11:
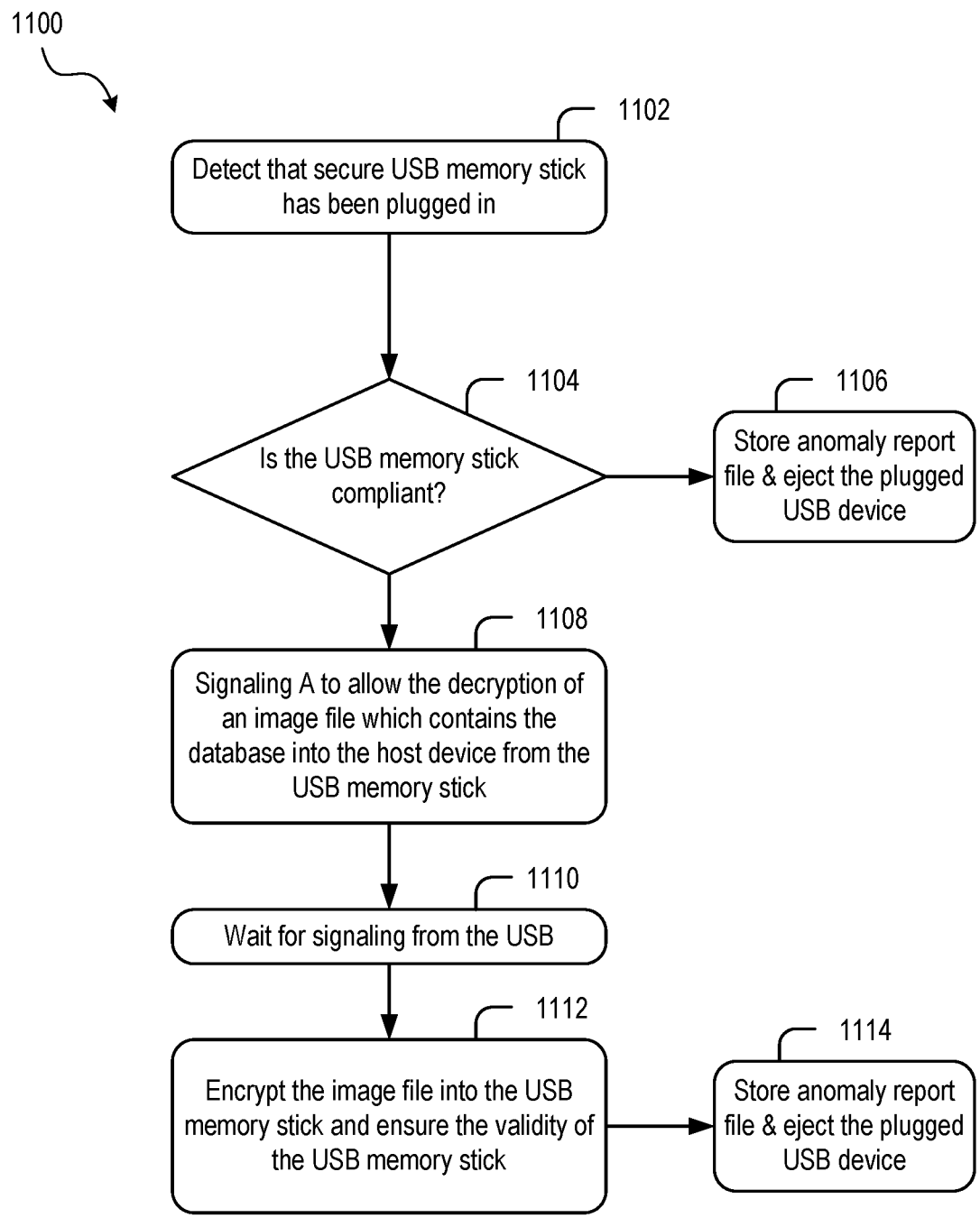
FIG. 11 shows an example secure dongle procedure performed by a host device according to some embodiments.

FIG. 11 shows an example secure dongle procedure 1100 performed by a host device according to some embodiments. In example method 1100, the secure dongle is a USB stick and the host device is therapy device 800 (FIG. 8) for illustration. In operation, the secure dongle could be some other type of storage device with processing capability. Similarly, the host device could be any host device configured to connect to and exchange information with the secure dongle.

At step 1102, the main module 802 of the therapy device 800 detects that a secure USB memory stick has been plugged into the therapy device 800.

Next, method 1100 proceeds to step 1104, where a determination is made as to whether the USB memory stick is valid and has a proprietary device class that is compliant with the therapy device. In some embodiments, the therapy device requires a USB stick with a special proprietary software interface rather than a standard, commercially-available USB stick.

If the USB memory stick is not valid or does not have a proprietary device class that is compliant with the therapy device, then method 1100 advances to step 1106, where the therapy device stores an anomaly report and ejects the USB stick.

But if the USB stick is valid and has a proprietary device class that is compliant with the therapy device, then method 1100 advances to step 1108, where the main module 802 sends a USB message, A, with a security code to the USB stick to obtain (i) a decryption key and (ii) an encrypted image file. Then, software running on the USB stick decrypts the image to be passed to the main module 802 to be mounted by signaling through a USB message. Other software processes running on the main module 802 access the mounted disk image like a part of a regular file system during step 1110.

After the main module 802 has finished accessing the mounted disk image, method 1100 advances to step 1112, where the main module 802 encrypts the mounted disk image and transfers the encrypted disk image to the USB stick via the USB interface.

Next, method 1100 advances to step 1114, where the main module 802 ejects the USB stick.

1.1.7 Secure Dongle Client Method

When the secure dongle is plugged into host, the host provides a confirmation signal using a message transferred through the host's communication interface to the secure dongle. If any of the received messages including the security code are incorrect, the secure dongle will reset itself until it is no longer attached to the host.

Figure 12:
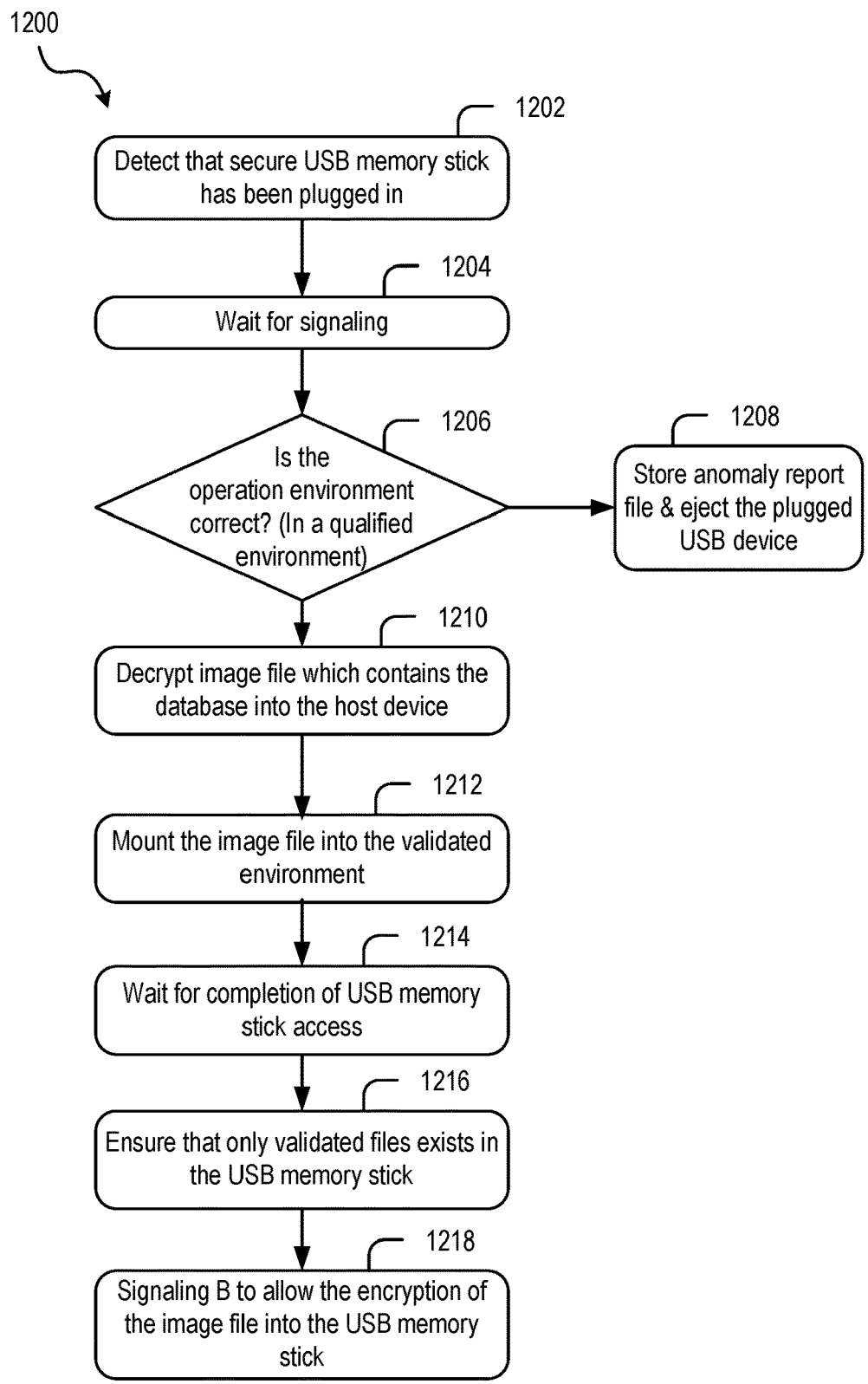
FIG. 12 shows an example of a secure dongle procedure performed by the secure dongle according to some embodiments.

FIG. 12 shows an example secure dongle method 1200 performed by the dongle according to some embodiments. In example method 1200, the secure dongle is a USB stick and the host device is therapy device 800 (FIG. 8) for illustration. In operation, the secure dongle could be some other type of storage device with processing capability.

Similarly, the host device could be any host device configured to connect to and exchange information with the secure dongle.

Method 1200 begins at step 1202, where the USB stick detects that it has been plugged in to the therapy device 800.

Next, method 1200 advances to step 1204, where the USB stick waits for signaling from the therapy device. In some embodiments, the USB stick waits to receive a USB message, A, from the therapy device 800.

Once the USB stick receives and validates the confirmation message from the therapy device 800, method 1200 advances to step 1206, where the USB stick determines whether it is connected to a valid host, e.g., whether it is connected to a valid therapy device 800 or perhaps other valid host, such as the computing and storage server 712 or one of the computer/tablets 714, 716 (FIG. 7).

If the host is not valid, then method 1200 advances to step 1208, where the USB stick stores and anomaly report and ejects itself from the host.

But if the host is valid, then method 1200 advances to step 1210, where the USB stick decrypts an image file that contains files for transferring to the host, which is the therapy device 800 in this example.

Next, method 1200 advances to step 1212, where the USB stick mounts and/or transfers the image file to/from the therapy device 800.

Next, method 1200 advances to step 1214, where the USB stick waits for an indication that files have been transferred to/from the therapy device 800.

Then, method 1200 advances to step 1216, where the USB stick confirms that only validated files from the therapy device 800 are present on the USB stick.

Finally, method 1200 advances to step 1218, where the USB stick encrypts the image file stored on the USB stick.

In operation, one difference between methods 1100 and 1200 performed by the host and secure dongle, respectively, and the method performed by standard, commercially-available USB sticks is that the methods 1100 and 1200 include validation and file encryption steps performed by the secure dongle (the USB stick in the example), whereas commercially-available USB sticks do not include software for performing host validation or file encryption/decryption, as far as the inventors are aware.

By including dongle validation and file encryption/decryption on the host and host validation and file encryption/decryption on the dongle, the methods 1100 and 1200 provide improved security over standard USB memory sticks, which is important for sensitive healthcare information like the patient treatment data, e.g., patient symptoms, treatment history, historical therapy configuration settings, etc., stored on the dongle and exchanged between the dongle and host.

CONCLUSIONS

While various aspects have been disclosed herein, other aspects will be apparent to those of skill in the art. The various aspects disclosed herein are for purposes of illustration and are not intended to be limiting, with the true scope being indicated by the following claims, along with the full scope of equivalents to which such claims are entitled. It is also to be understood that the terminology used herein is for the purpose of describing particular example embodiments only, and is not intended to be limiting. For example, while the disclosed example embodiments focus on particular implementations of therapy devices for treating chronic pain, some aspects of the disclosed systems and methods may be equally applicable to other systems and devices in other fields of use.

What is claimed is:

1. A system comprising:
   one or more processing elements;
   circuitry configured to generate and apply electrical stimulation signals to a patient via one or more sets of electrodes; and
   tangible, non-transitory computer-readable media comprising instructions stored therein, wherein the instructions, when executed by the one or more processing elements, cause the system to perform functions comprising:
   generating one or more random electrical stimulation signals in a frequency range between about 5 Hz and about 2 KHz, wherein at least one of the one or more random electrical stimulation signals is based on a plurality of non-pulsed waveforms from a library of non-pulsed waveforms; and
   applying the one or more random electrical stimulation signals to a patient via the circuitry.

2. The system of claim 1, wherein each waveform of the plurality of non-pulsed waveforms has a rise time greater than about 10 microseconds.

3. The system of claim 1, wherein the functions further comprise:
   controlling an individual waveform to have a randomized RMS voltage between a configurable lower RMS voltage and a configurable upper RMS voltage.

4. The system of claim 1, wherein the functions further comprise:
   controlling at least one of the one or more random electrical stimulation signal to limit RMS current applied to the patient, wherein the RMS current applied to the patient is less than or equal to a configurable maximum RMS current limit.

5. The system of claim 3, wherein the functions further comprise:
   setting at least one of the lower RMS voltage and the upper RMS voltage of the waveform for the patient based at least in part on an analysis of a plurality of quantitative pain metrics for the patient.

6. The system of claim 3, wherein the functions further comprise:
   setting the upper RMS voltage and lower RMS voltage to define a range of RMS voltage levels expected to be effective for treating a chronic pain symptom for the patient.

7. The system of claim 1, wherein the functions further comprise:
   receiving one or more of an upper RMS voltage level setting, a lower RMS voltage level setting, and a maximum RMS current level setting for one of the one or more random waveforms;
   determining whether any of the received upper RMS voltage level setting, lower RMS voltage level setting, and maximum RMS current level setting would, if implemented, either (i) increase a likelihood that the electrical stimulation signal will cause the patient to experience pain or discomfort or (ii) reduce a likelihood that the electrical stimulation signal will be effective for treating a chronic pain symptom for the patient; and
   in response to determining that at least one of the received upper RMS voltage level setting, lower RMS voltage level setting, and maximum RMS current level setting would, if implemented, increase a likelihood that the electrical stimulation signal will cause the patient to experience pain or discomfort or reduce the likelihood that the electrical stimulation signal will be effective for treating a chronic pain symptom for the patient, overriding at least one of the received upper RMS voltage level setting, lower RMS voltage level setting, or maximum RMS current level setting with a corresponding different setting determined by the system to one or both (i) not increase a likelihood that the electrical stimulation signal will cause the patient to experience pain or discomfort or (i) not reduce the likelihood that the electrical stimulation signal will be effective for treating a chronic pain symptom for the patient.

8. The system of claim 1, wherein the functions further comprise generating the plurality of non-pulsed waveforms, wherein generating the plurality of non-pulsed waveforms comprises, for an individual waveform:
  determining one or more waveform attributes for the waveform, the waveform attributes comprising (i) a random number of segments for the waveform, (ii) a random positive peak voltage for the waveform, (iii) a random location in the waveform for the positive peak voltage, (iv) a random negative peak voltage for the waveform, (v) a random location in the waveform for the negative peak voltage, (vi) a random location in the waveform for each waveform segment, and (vii) a random slope for each waveform segment; and
  generating the waveform according to the one or more determined waveform attributes.

9. The system of claim 1, wherein an individual non-pulsed waveform comprises (i) a positive peak voltage that is limited to a maximum positive peak voltage, and (ii) a negative peak voltage that is limited to a maximum negative peak voltage.

10. The system of claim 1, wherein the circuitry configured to generate and apply electrical stimulation signals to a patient via one or more sets of electrodes comprises:
  waveform generation circuitry configured to generate the plurality of non-pulsed waveforms;
  signal generation circuitry configured to generate one or more random electrical stimulation signals based on the plurality of non-pulsed waveforms; and
  therapy application circuitry configured to receive at least one of the one or more random electrical stimulation signal from the signal generation circuitry, condition the random electrical stimulation signal for application to the patient, and apply the conditioned random electrical stimulation signal to the patient.

11. The system of claim 8, wherein an individual waveform has a randomized RMS voltage between a configurable lower RMS voltage and a configurable upper RMS voltage, and wherein the system further comprises:
  one or more communication interfaces configured to transfer system configuration parameters comprising one or more of the waveform attributes, the upper RMS voltage, and the lower RMS voltage used during a therapy session between the system and a database configured for storing system configuration parameters.

12. The system of claim 11, wherein an initial set of system configuration parameters for use during an initial therapy session for the patient is based on a clinician's assessment of one or more of the patient's symptoms and an initial set of quantitative pain metrics provided by the patient, and wherein one or more subsequent sets of system configuration parameters for use during one or more subsequent therapy sessions for the patient are based on the clinician's observations of therapy results and one or more subsequent sets of quantitative pain metrics provided by the patient.

13. The system of claim 11, wherein the one or more communication interfaces is configured to connect the system to one or both of a secure dongle or a secure cloud-based computing system.

14. A device comprising:
  one or more processing elements;
  circuitry configured to generate and apply electrical stimulation signals to a patient via one or more sets of electrodes; and
  tangible, non-transitory computer-readable media comprising instructions stored therein, wherein the instructions, when executed by the one or more processing elements, cause the system to perform functions comprising:
    generating one or more random electrical stimulation signals in a frequency range between about 5 Hz and about 2 KHz, wherein at least one of the one or more electrical stimulation signals is based on a plurality of waveforms from a library of non-pulsed waveforms; and
    applying the one or more random electrical stimulation signals to a patient via the circuitry.

15. The device of claim 14, wherein each waveform of the plurality of non-pulsed waveforms has a rise time greater than about 10 microseconds.

16. The device of claim 14, wherein the functions further comprise:
  controlling an individual waveform to have a randomized RMS voltage between a configurable lower RMS voltage and a configurable upper RMS voltage.

17. The device of claim 14, wherein the functions further comprise:
  controlling at least one of the one or more random electrical stimulation signal to limit RMS current applied to the patient, wherein the RMS current applied to the patient is less than or equal to a configurable maximum RMS current limit.

18. The device of claim 16, wherein the functions further comprise:
  setting at least one of the lower RMS voltage and the upper RMS voltage of the waveform for the patient based at least in part on an analysis of a plurality of quantitative pain metrics for the patient.

19. The device of claim 16, wherein the functions further comprise:
  setting the upper RMS voltage and lower RMS voltage to define a range of RMS voltage levels expected to be effective for treating a chronic pain symptom for the patient.

20. The device of claim 14, wherein the functions further comprise generating the plurality of non-pulsed waveforms, wherein generating the plurality of non-pulsed waveforms comprises, for an individual waveform:
  determining one or more waveform attributes for the waveform, the waveform attributes comprising (i) a random number of segments for the waveform, (ii) a random positive peak voltage for the waveform, (iii) a random location in the waveform for the positive peak voltage, (iv) a random negative peak voltage for the waveform, (v) a random location in the waveform for the negative peak voltage, (vi) a random location in the waveform for each waveform segment, and (vii) a random slope for each waveform segment; and generating the waveform according to the one or more determined waveform attributes.

\* \* \* \* \*